United States Patent [19]
Yokoi et al.

[11] Patent Number: 5,498,780
[45] Date of Patent: Mar. 12, 1996

[54] PLATINUM COMPLEX AND MALIGNANT TUMOR TREATING DRUG CONTAINING THE SAME

[75] Inventors: Koichi Yokoi; Kinichi Mogi; Hidehiko Kohya; Mari Ohtsuka; Hiroyuki Mizuno; Susumu Sato; Tadayuki Kuraishi, all of Chiba, Japan

[73] Assignee: SS Pharmaceutical Co., Ltd., Tokyo, Japan

[21] Appl. No.: 454,825

[22] Filed: May 31, 1995

[30] Foreign Application Priority Data

Jun. 3, 1994 [JP] Japan ................................. 6-122209

[51] Int. Cl.⁶ ............................ A61K 31/28; C07F 15/00
[52] U.S. Cl. ............................................ 514/492; 556/137
[58] Field of Search ............................. 556/137; 514/492

[56] References Cited

U.S. PATENT DOCUMENTS

| | | | |
|---|---|---|---|
| 4,376,782 | 3/1983 | Turkevich et al. | 424/287 |
| 4,687,780 | 8/1987 | Barnard | 514/492 |
| 4,748,254 | 5/1988 | Cheltsov-Bebutov et al. | 549/206 |
| 4,760,155 | 7/1988 | Heffernan et al. | 556/136 |

FOREIGN PATENT DOCUMENTS 0098135  11/1984  European Pat. Off.

OTHER PUBLICATIONS

Konstantinova et al., Chemical Abstracts, vol. 94, No. 10, Abs. No. 72415c (1981).
Chemical Abstracts, vol. 96, No. 8, Abstract No. 61976b (1982).

*Primary Examiner*—Porfirio Nazario-Gonzales
*Attorney, Agent, or Firm*—Sughrue, Mion, Zinn, Macpeak & Seas

[57] ABSTRACT

A diamine-platinum complex represented by the following formula (1):

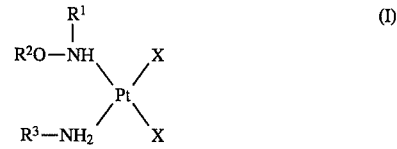

wherein the all definitions are defined in the disclosure, and a malignant tumor treating drug which contains the above complex as an active ingredient. The diamine-platinum complex has a high water solubility and an excellent antitumor effect.

9 Claims, No Drawings

PLATINUM COMPLEX AND MALIGNANT TUMOR TREATING DRUG CONTAINING THE SAME

FIELD OF THE INVENTION

This invention relates to a novel platinum complex having an excellent antitumor effect and a malignant tumor treating drug which contains the platinum complex.

BACKGROUND OF THE INVENTION

Various antitumor substances have been developed for use in the treatment of malignant tumors which are now the most highest cause of death.

Among these substances, cisplatin, an antitumor platinum compound, has a broad range of antitumor spectrum and takes an important role in the chemotherapy of various tumors.

However, cisplatin has a problem of causing side effects such as renal toxicity, blood toxicity, digestive organ disorder, nervous toxicity and the like. In consequence, antitumor drugs having low toxicities and high antitumor effects have been developed.

For example, antitumor effects of diamine-platinum(II) compounds represented by formula cis-[PtAA'Y$_2$] (wherein A and A' are amines differing from each other and Y represents a leaving group such as a halogen atom, a carboxylate or the like) have been reported in U.S. Pat. No. 4,329,299, JP-A-60-109521 (the term "JP-A" as used herein means an "unexamined published Japanese patent application"), JP-A-61-15892, JP-A-61-83194, JP-A-2-96523 and JP-A-2-4797.

These antitumor substances, however, have disadvantages in that their effects and safety are not always satisfactory and their administration by injection are limited because of their low solubility in water.

SUMMARY OF THE INVENTION

In consequence, it is therefore an object of the present invention to provide a platinum complex which has excellent antitumor effects, high safety and good water solubility and a malignant tumor treating drug that contains the platinum complex.

In view of the above, the present inventors have conducted intensive studies and found that a diamine-platinum complex represented by the following formula (1) shows excellent antitumor effects and has high safety and a good solubility in water. The present invention has been accomplished on the basis of this finding.

Thus, according to the present invention, there is provided a diamine-platinum complex represented by the following formula (1):

$$\begin{array}{c} R^1 \\ | \\ R^2O-NH \diagdown \diagup X \\ Pt \\ \diagup \diagdown \\ R^3-NH_2 \quad X \end{array} \quad (I)$$

wherein $R^1$, $R^2$ and $R^3$ may be the same or different from one another, and each represents hydrogen atom, a straight-chain or branched alkyl group, a cycloalkyl group or an aralkyl group, and X is a halogen atom, or two X groups bind to each other to form a malonic acid residue which may have a substituent, with the proviso that $R^1$, $R^2$ and $R^3$ are not hydrogen atoms at the same time.

The present invention also provides a drug for use in the treatment of malignant tumors, which contains the diamine-platinum complex represented by the above formula (1) as an active ingredient.

Other objects and advantages of the present invention will be made apparent as the description progresses.

DETAILED DESCRIPTION OF THE INVENTION

In the diamine-platinum complex of the present invention represented by the above formula (1), preferred examples of the alkyl group of $R^1$ to $R^3$ are those which have 1 to 9 carbon atoms, such as methyl, ethyl, straight-chain or branched propyl, butyl, pentyl, hexyl, heptyl, octyl, nonyl and the like groups, more preferably methyl, ethyl, straight-chain or branched propyl, butyl, pentyl and hexyl. Preferred examples of cycloalkyl group are those which have 3 to 9 carbon atoms, such as cyclopropyl, cyclobutyl, cyclopentyl, cyclohexyl, cycloheptyl, cyclooctyl, cyclononyl and the like groups, of which cyclobutyl, cyclopentyl and cyclohexyl are more preferred. Preferred examples of the aralkyl group include benzyl, 3-hydroxybenzyl, 4-hydroxybenzyl, phenetyl, diphenylmethyl, trityl and the like groups, of which benzyl group is more preferred. In formula (1), examples of the halogen atom represented by X include fluorine, chlorine, bromine and iodine. Examples of the malonic acid residue formed by two X groups are those represented by the following formulae.

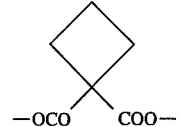

The diamine-platinum complex (1) of the present invention can be produced in accordance, for example, with the following reaction scheme which is a partial modification of a known method (Canadian Journal of Chemistry, vol. 64, p. 1894, 1986).

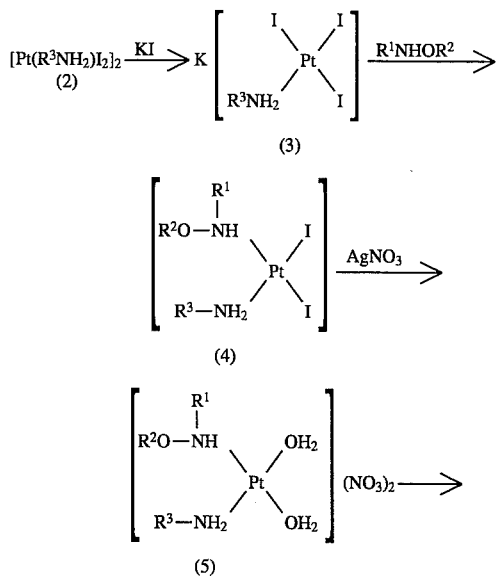

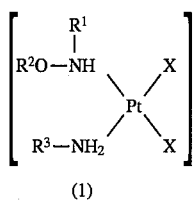

(1)

In the above formulae, $R^1$, $R^2$, $R^3$ and X are as defined in the foregoing.

That is, a platinum complex (1) of interest of the present invention can be obtained by allowing a Pt compound (2) to react with potassium iodide, allowing the resulting compound (3) to react with an amine represented by $R^1NHOR^2$, allowing the resulting compound (4) to react with silver nitrate to form a diaquo complex (5) and then allowing the diaquo complex (5) in aqueous solution to react with a malonic acid or a salt thereof or a halogen atom-containing acid or a salt thereof.

More particularly, it is desirable to produce the platinum complex of the present invention in the following manner.

Firstly, 1 mole of the compound (2) is allowed to react with preferably 2 to 20 moles, more preferably 4 to 10 moles, of potassium iodide. This reaction is carried out by stirring the reaction mixture at a temperature of from 0° to 100° C., preferably from room temperature to 60° C., for generally 20 minutes to 2 hours. Preferably, the solvent to be used in this reaction is water or a mixture of water and ethanol.

Since the thus obtained compound (3) is highly soluble in water in comparison with the compound (2), the subsequent reaction can be carried out markedly smoothly.

Next, the thus obtained compound (3) is allowed to react with an amine represented by $R^1NHOR^2$. This amine is used by adding an alkali hydroxide aqueous solution to its hydrochloric acid salt. The alkali hydroxide may be used preferably in an amount of about 0.5 to 1 mole per 1 mole of the amine, and the amine may be used preferably in an amount of 1 to 4 moles per 1 mole of the compound (3). The reaction of the compound (3) with the amine is carried out by stirring the reaction mixture at a temperature of preferably from 0° to 40° C. more preferably from 0° to 20° C., for generally about 10 minutes to 2 hours.

The compound (4) can be obtained in this manner, but it can also be obtained directly from the compound (2). In the latter case, it is desirable to carry out the reaction by adding 0.1 to 10 moles, preferably 0.2 to 5 moles of potassium iodide per 1 mole of the compound (2) and further adding about 2 to 6 moles of $R^1NHOR^2$ hydrochloride, which has been mixed with 0.5 to 1 mole of an alkali hydroxide aqueous solution, per 1 mole of the compound (2). This reaction is carried out by stirring the reaction mixture at a temperature of from 0° to 40° C., preferably from 0° to 20° C., for generally 10 minutes to 4 hours.

The compound (5) is obtained by suspending the thus obtained compound (4) in water, adding silver nitrate to the suspension to proceed reaction while stirring the mixture at a temperature of preferably from 0° to 60° C., more preferably from 0° to 40° C., for a period of generally from 30 minutes to 2 hours. In this case, silver nitrate is used preferably in an amount of about 1.8 to 2 moles per 1 mole of the compound (4). After completion of the reaction, the precipitates of silver iodide is removed by filtration to obtain aqueous solution of the diaquo complex (5).

Thereafter, the diamine-platinum complex (1) of interest is obtained by allowing the thus obtained diaquo complex (5) to react with dilute hydrochloric acid or sodium chloride, potassium chloride or the like salt or malonic acid (salt) or a substituted malonic acid (salt). Dilute hydrochloric acid or the salt may be used in an amount of preferably from about 1 to 20 moles, more preferably from about 2 to 10 moles, per 1 mole of the diaquo complex, and the reaction may be carried out at a temperature of preferably from about 0° to 60° C., more preferably from about 10° to 40° C., for a period of preferably from 20 minutes to 2 hours.

After completion of the reaction, the reaction product is subjected to purification in a conventional manner to give thereby the diamine-platinum complex (1) in a high purity.

The thus obtained diamine-platinum complex (1) is useful as a malignant tumor treating drug, because it shows an excellent antitumor effect, is low in toxicity and has a high solubility in water.

When the diamine-platinum complex (1) is administered to mammals including human as a malignant tumor treating agent, it is desirable to make the complex into a pharmaceutical composition by combining it with a pharmaceutically acceptable carrier. Examples of such pharmaceutical composition include a composition for intravenous injection, intramuscular injection, tumor injection or the like use, a composition for oral administration use, a composition for rectal administration use and the like, of which the composition for injection use is preferred. Examples of the pharmaceutically acceptable carrier to be used herein include distilled water for injection use, physiological saline, a buffer solution and the like.

The dose of the malignant tumor treating drug of the present invention varies depending on the conditions, age, body weight and the like of each patient. In the case of injection, the dose may be preferably from 3 mg/m² to 150 mg/m² per day as the diamine-platinum complex (1), and the daily dose may be divided into 1 to 3 doses per day.

The following examples are provided to further illustrate the present invention. It is to be understood, however, that the examples are for purpose of illustration only and are not intended as a definition of the limits of the invention.

EXAMPLE 1

(Compound No. 1)

A 4.66 g (5 mmol) portion of $[Pt(NH_3)I_2]_2$ was suspended in 50 ml of water, and 8.3 g (50 mmol) of potassium iodide was added to the suspension, followed by stirring the resulting mixture at 60° C. for 30 minutes to obtain a $K[Pt(NH_3)I_3]$ aqueous solution ($^{195}Pt$ NMRδ:–4228). To this aqueous solution was added dropwise 1.26 g (15 mmol) of N-methylhydroxylamine hydrochloride dissolved in 10 ml of 1N sodium hydroxide over 20 minutes while stirring and cooling in an ice bath. Yellow crystals thus precipitated were collected by filtration, washed with water and then dried to obtain 3.01 g of cis-diiodoammine (N-methylhydroxylamine)platinum(II) as crystals (yield: 58.7%).

Melting point: 105°–110° C. (decomposition) Elemental analysis data: calcd. (%): C, 2.34; H, 1.57; N, 5.46 found (%): C, 2.69; H, 1.75; N, 5.37

A 1.54 g (3 mmol) portion of the thus obtained cis-diiodoammine (N-methylhydroxylamine)platinum(II) was suspended in 20 ml of water, and 1.02 g (6 mmol) of silver nitrate was added to the suspension, followed by stirring the resulting mixture at room temperature for 60 minutes. After the reaction, the precipitated silver iodide was removed by filtration, and the resulting filtrate was mixed with 0.70 g (12 mmol) of sodium chloride and subjected to 1 hour of reaction at room temperature. When the reaction solution was concentrated to about 3 ml and allowed to stand at 0° C. for 3 hours, yellow crystals were precipitated. These crystals were collected by filtration, washed with water and then dried to obtain 0.53 g of cis-dichloroammine (N-methylhydroxylamine)platinum(II) (Compound No. 1) as crystals (yield: 53.9%).

Melting point: 134°–137° C. (decomposition) $^{195}$Pt NMR (DMF-$d_7$) δ: −2184 $^{13}$C NMR (DMF-$d_7$) δ: 47.8 Elemental analysis data: calcd. (%): C, 3.64; H, 2.44; N, 8.49 found (%): C, 3.57; H, 2.48; N, 8.72

EXAMPLE 2

(Compound No. 2)

The procedure of Example 1 was repeated except that 1.26 g (15 mmol) of N-methylhydroxylamine hydrochloride was replaced by 1.26 g (15 mmol) of O-methylhydroxylamine hydrochloride, thereby obtaining 4.11 g of cis-diiodoammine (O-methylhydroxylamine)platinum(II) as crystals (yield: 80.1%).

Melting point: 117°–120° C. (decomposition) Elemental analysis data: calcd. (%): C, 2.34; H, 1.57; N, 5.46 found (%): C, 2.40; H, 1.32; N, 5.31

Using a 1.54 g (3 mmol) portion of the thus obtained cis-diiodoammine (O-methylhydroxylamine)platinum(II), the procedure of Example 1 was repeated to obtain 0.64 g of cis-dichloroammine (O-methylhydroxylamine)platinum(II) (Compound No. 2) as yellow crystals (yield: 64.8%).

Melting point: 148°–149° C. (decomposition) $^{195}$Pt NMR (DMF-$d_7$) δ: −2249 $^{13}$C NMR (DMF-$d_7$) δ: 62.1 Elemental analysis data: calcd. (%): C, 3.64; H, 2.44; N, 8.49 found (%): C, 3.52; H, 2.45; N, 8.76

EXAMPLE 3

(Compound No. 3)

The procedure of Example 1 was repeated except that 1.26 g (15 mmol) of N-methylhydroxylamine hydrochloride was replaced by 1.68 g (15 mmol) of N-isopropylamine hydrochloride dissolved in 10 ml of 1N sodium hydroxide, which was added dropwise over 1 hour while stirring the reaction mixture in an ice bath. Yellow crystals thus formed were collected by filtration, washed with water and then dried to obtain 3.75 g of cis-diiodoammine (N-isopropylhydroxylamine)platinum(II) (yield: 69.4%).

Melting point: 106°–110° C. (decomposition) Elemental analysis data: calcd. (%): C, 6.66; H, 2.24; N, 5.18 found (%): C, 6.51; H, 2.13; N, 5.31

Using a 1.62 g (3 mmol) portion of the thus obtained cis-diiodoammine (N-isopropylhydroxylamine)platinum(II), the procedure of Example 1 was repeated to obtain 0.77 g of cis-dichloroammine (N-isopropylhydroxylamine)platinum(II) (Compound No. 3) as yellow crystals (yield: 71.5%).

Melting point: 153°–155° C. (decomposition) $^{195}$Pt NMR (DMF-$d_7$) δ: −2194 $^{13}$C NMR (DMF-$d_7$) δ: 18.9, 20.0, 60.3 Elemental analysis data: calcd. (%): C, 10.06; H, 3.38; N, 7.82 found (%): C, 9.84; H, 3.29; N, 7.72

EXAMPLE 4

(Compound No. 4)

The procedure of Example 1 was repeated except that 1.26 g (15 mmol) of N-methylhydroxylamine hydrochloride was replaced by 2.28 g (15 mmol) of N-cyclohexylhydroxylamine hydrochloride dissolved in 35 ml of methanol to which was subsequently added 10 ml of 1N sodium hydroxide. The resulting solution was added dropwise a K[Pt(NH$_3$)I$_3$] aqueous solution under cooling in an ice bath and yellow crystals formed after 2 hours of stirring were collected by filtration, washed with water and then dried to obtain 3.12 g of cis-diiodoammine (N-cyclohexylhydroxylamine)platinum(II) (yield: 53.7%).

Melting point: 113°–115° C. (decomposition) Elemental analysis data: calcd. (%): C, 12.40; H, 2.78; N, 4.82 found (%): C, 12.19; H, 2.75; N, 4.58

Using a 1.74 g (3 mmol) portion of the thus obtained cis-diiodoammine (N-cyclohexylhydroxylamine)platinum(II), the procedure of Example 1 was repeated to obtain 0.96 g of cis-dichloroammine (N-cyclohexylhydroxylamine)platinum(II) (Compound No. 4) as yellow crystals (yield: 80.4%).

Melting point: 143°–145° C. (decomposition) $^{195}$Pt NMR (DMF-$d_7$) δ: −2192 $^{13}$C NMR (DMF-$d_7$) δ: 25.4, 25.4, 26.3, 29.9, 30.9, 67.6 Elemental analysis data: calcd. (%): C, 18.10; H, 4.05; N, 7.03 found (%): C, 17.77; H, 4.17; N, 6.93

EXAMPLE 5

(Compound No. 5)

The procedure of Example 1 was repeated except that 1.26 g (15 mmol) of N-methylhydroxylamine hydrochloride was replaced by 1.46 g (15 mmol) of O-ethylhydroxylamine hydrochloride, thereby obtaining 3.68 g of cis-diiodoammine (O-ethylhydroxylamine)platinum(II) as crystals (yield: 68.9%)

Melting point: 103°–108° C. (decomposition) Elemental analysis data: calcd. (%): C, 4.56; H, 1.91; N, 5.32 found (%): C, 4.31; H, 1.81; N, 5.31

Using a 1.58 g (3 mmol) portion of the thus obtained cis-diiodoammine (O-ethylhydroxylamine)platinum(II), the procedure of Example 1 was repeated to obtain 0.80 g of cis-dichloroammine (O-ethylhydroxylamine)platinum(II) (Compound No. 5) as yellow crystals (yield: 77.4%).

Melting point: 180°–183° C. (decomposition) $^{195}$Pt NMR (DMF-$d_7$) δ: −2242 $^{13}$C NMR (DMF-$d_7$) δ: 13.3, 71.2 Elemental analysis data: calcd. (%): C, 6.98; H, 2.93; N, 8.14 found (%): C, 6.78; H, 3.15; N, 8.08

EXAMPLE 6

(Compound No. 6)

The procedure of Example 1 was repeated except that 1.26 g (15 mmol) of N-methylhydroxylamine hydrochloride was replaced by 1.46 g (15 mmol) of N,O-dimethylhydroxylamine hydrochloride, thereby obtaining 3.30 g of cis-diiodoammine (N,O-dimethylhydroxylamine)platinum(II) as crystals (yield: 62.6%).

Melting point: 105°–111° C. (decomposition) Elemental analysis data: calcd. (%): C, 4.56; H, 1.91; N, 5.32 found (%): C, 4.35; H, 1.76; N, 5.28

Using a 1.58 g (3 mmol) portion of the thus obtained cis-diiodoammine (N,O-dimethylhydroxylamine)platinum(II), the procedure of Example 1 was repeated to obtain 0.63 g of cis-dichloroammine (N,O-dimethylhydroxylamine)platinum(II) (Compound No. 6) as yellow crystals (yield: 60.7%).

Melting point: 158°–164° C. (decomposition) $^{195}$Pt NMR (DMF-$d_7$) δ: −2234 $^{13}$C NMR (DMF-$d_7$) δ: 46.3, 59.8 Elemental analysis data: calcd. (%): C, 6.98; H, 2.93; N, 8.14 found (%): C, 6.88; H, 3.00; N, 8.29

EXAMPLE 7

(Compound No. 7)

The procedure of Example 1 was repeated except that 1.26 g (15 mmol) of N-methylhydroxylamine hydrochloride was replaced by 1.88 g (15 mmol) of O-tert-butylhydroxylamine hydrochloride, thereby obtaining 3.82 g of cis-diiodoammine (O-tert-butylhydroxylamine)platinum(II) as crystals (yield: 68.9%).

Melting point: 105°–108° C. (decomposition) Elemental analysis data: calcd. (%): C, 8.66; H, 2.54; N, 5.05 found (%): C, 8.61; H, 2.36; N, 4.91

Using a 1.67 g (3 mmol) portion of the thus obtained cis-diiodoammine (O-tert-butylhydroxylamine)platinum(II), the procedure of Example 1 was repeated to obtain 0.93 g of cis-dichloroammine (O-tert-butylhydroxylamine)platinum(II) (Compound No. 7) as yellow crystals (yield: 83.0%).

Melting point: 204°–209° C. (decomposition) $^{195}$Pt NMR (DMF-$d_7$) δ: −2213 $^{13}$C NMR (DMF-$d_7$) δ: 26.2, 26.2, 26.2, 80.9 Elemental analysis data: calcd. (%): C, 12.91; H, 3.79; N, 7.53 found (%): C, 13.03; H, 3.84; N, 7.18

EXAMPLE 8

(Compound No. 8)

The procedure of Example 1 was repeated except that 1.26 g (15 mmol) of N-methylhydroxylamine hydrochloride was replaced by 1.67 g (15 mmol) of O-propylhydroxylamine hydrochloride, thereby obtaining 2.86 g of cis-diiodoammine (O-propylhydroxylamine)platinum(II) as crystals (yield: 52.9%).

Melting point: 108°–113° C. (decomposition) Elemental analysis data: calcd. (%): C, 6.66; H, 2.24; N, 5.18 found (%): C, 6.72; H, 2.24; N, 5.14

Using a 1.62 g (3 mmol) portion of the thus obtained cis-diiodoammine (O-propylhydroxylamine)platinum(II), the procedure of Example 1 was repeated to obtain 0.78 g of cis-dichloroammine (O-propylhydroxylamine)platinum(II) (Compound No. 8) as yellow crystals (yield: 72.4%).

Melting point: 166°–172° C. (decomposition) $^{195}$Pt NMR (DMF-$d_7$) δ: −2241 $^{13}$C NMR (DMF-$d_7$) δ: 10.6, 21.4, 76.2 Elemental analysis data: calcd. (%): C, 10.06; H, 3.38; N, 7.82 found (%): C, 9.98; H, 3.34; N, 7.84

EXAMPLE 9

(Compound No. 9)

The procedure of Example 1 was repeated except that 1.26 g (15 mmol) of N-methylhydroxylamine hydrochloride was replaced by 2.28 g (15 mmol) of O-cyclohexylhydroxylamine hydrochloride, thereby obtaining 3.47 g of cis-diiodoammine (O-cyclohexylhydroxylamine)platinum(II) (yield: 59.7%).

Using a 1.74 g (3 mmol) portion of the thus obtained cis-diiodoammine (O-cyclohexylhydroxylamine)platinum(II), the procedure of Example 1 was repeated to obtain 0.66 g of cis-dichloroammine (O-cyclohexylhydroxylamine)platinum(II) (yield: 55.2%).

EXAMPLE 10

(Compound No. 10)

The procedure of Example 1 was repeated except that 1.26 g (15 mmol) of N-methylhydroxylamine hydrochloride was replaced by 2.39 g (15 mmol) of O-benzylhydroxylamine hydrochloride, thereby obtaining 4.93 g of cis-diiodoammine (O-benzylhydroxylamine)platinum(II) (yield: 82.5%).

Using a 1.77 g (3 mmol) portion of the thus obtained cis-diiodoammine (O-benzylhydroxylamine)platinum(II), the procedure of Example 1 was repeated to obtain 0.73 g of cis-dichloroammine (O-benzylhydroxylamine)platinum(II) (yield: 60.3%).

EXAMPLE 11

(Compound No. 11)

The procedure of Example 1 was repeated except that 1.26 g (15 mmol) of N-methylhydroxylamine hydrochloride was replaced by 2.09 g (15 mmol) of N-neopentylhydroxylamine hydrochloride, thereby obtaining 3.58 g of cis-diiodoammine (N-neopentylhydroxylamine)platinum(II) as crystals (yield: 62.9%).

Using a 1.71 g (3 mmol) portion of the thus obtained cis-diiodoammine (N-neopentylhydroxylamine)platinum(II), the procedure of Example 1 was repeated to obtain 0.75 g of cis-dichloroammine (N-neopentylhydroxylamine)platinum(II) as yellow crystals (yield: 65.1%).

EXAMPLE 12

(Compound No. 12)

A 5.08 g (5 mmol) portion of [Pt(isopropylamine)$I_2$]$_2$ was suspended in a mixture solution consisting of 30 ml of water and 55 ml of ethanol, and 0.83 g (5 mmol) of potassium iodide was added to the suspension. To the resulting mixture was added dropwise 1.46 g (15 mmol) of O-ethylhydroxylamine hydrochloride dissolved in 10 ml of 1N sodium hydroxide over 3 hours while stirring the mixture at room temperature. After the reaction, the crystals thus formed were collected by filtration, washed with water and then dried to obtain 3.86 g of cis-diiodo(isopropylamine) (O-ethylhydroxylamine)platinum(II) as yellow crystals (yield: 67.9%).

Using a 1.71 g (3 mmol) portion of the thus obtained cis-diiodo(isopropylamine) (O-ethylhydroxylamine)platinum(II), the procedure of Example 1 was repeated to obtain 0.54 g of cis-dichloro(isopropylamine) (O-ethylhydroxylamine)platinum(II) (yield: 46.4%).

EXAMPLE 13

(Compound No. 13)

The procedure of Example 12 was repeated except that [Pt(isopropylamine)$I_2$]$_2$ was replaced by 5.48 g (5 mmol) of [Pt(cyclohexylamine)$I_2$]$_2$, thereby obtaining 5.29 g of cis-diiodo(cyclohexylamine) (O-ethylhydroxylamine)platinum(II) (yield: 86.8%).

Using a 1.83 g (3 mmol) portion of the thus obtained cis-diiodo(cyclohexylamine) (O-ethylhydroxylamine)platinum(II), the procedure of Example 12 was repeated to obtain 0.83 g of cis-dichloro(cyclohexylamine) (O-ethylhydroxylamine)platinum(II) (yield: 64.6%).

EXAMPLE 14

(Compound No. 14)

The procedure of Example 12 was repeated except that O-ethylhydroxylamine hydrochloride was replaced by 1.88 g (15 mmol) of O-tert-butylhydroxylamine hydrochloride, thereby obtaining 5.37 g of cis-diiodo(isopropylamine) (O-tert-butylhydroxylamine)platinum(II) (yield: 89.9%).

Using a 1.79 g (3 mmol) portion of the thus obtained cis-diiodo(isopropylamine) (O-tert-butylhydroxylamine)platinum(II), the procedure of Example 1 was repeated to obtain 0.79 g of cis-dichloro(isopropylamine) (O-tert-butylhydroxylamine)platinum(II) (yield: 63.8%).

EXAMPLE 15

(Compound No. 15)

A 1.58 g (3 mmol) portion of cis-diiodoammine (O-ethylhydroxylamine)platinum(II) was suspended in 20 ml of water, and 1.02 g (6 mmol) of silver nitrate was added to the suspension, followed by stirring the resulting mixture at room temperature for 60 minutes. After the reaction, the precipitated silver iodide was removed by filtration, and the resulting filtrate was mixed with 0.58 g (4 mmol) of 1,1-cyclobutanedicarboxylic acid dissolved in 6 ml of 1N sodium hydroxide. After 60 minutes of reaction at room temperature, the reaction solution was evaporated to dryness under a reduced pressure, and the resulting residue was recrystallized from ethanol to obtain 0.61 g of (1,1-cyclobutane dicarboxylate)ammine (O-ethylhydroxylamine)platinum(II) as colorless crystals (yield: 49.0%).

EXAMPLE 16

(Compound No. 16)

The procedure of Example 15 was repeated except that 1.62 g (3 mmol) of cis-diiodoammine (O-propylhydroxylamine)platinum(II) was used instead of cis-diiodoammine (O-ethylhydroxylamine)platinum(II), thereby obtaining 0.53 g of (1,1-cyclobutane dicarboxylate)ammine (O-propylhydroxylamine)platinum(II) as colorless crystals (yield: 41.2%).

EXAMPLE 17

(Compound No. 17)

The procedure of Example 15 was repeated except that 1.67 g (3 mmol) of cis-diiodoammine (O-tert-butylhydroxylamine)platinum(II) was used instead of cis-diiodoammine (O-ethylhydroxylamine)platinum(II), thereby obtaining 0.61 g of (1,1-cyclobutane dicarboxylate)ammine (O-tert-butylhydroxylamine)platinum(II) as colorless crystals (yield: 54.8%).

EXAMPLE 18

(Compound No. 18)

The procedure of Example 12 was repeated except that [Pt(isopropylamine)I$_2$]$_2$ was replaced by 4.80 g (5 mmol) of [Pt(methylamine)I$_2$]$_2$, thereby obtaining 3.48 g of cis-diiodo(methylamine) (O-ethylhydroxylamine)platinum(II) (yield: 64.4%).

Using a 1.62 g (3 mmol) portion of the thus obtained cis-diiodo(methylamine) (O-ethylhydroxylamine)platinum(II), the procedure of Example 12 was repeated to obtain 0.66 g of cis-dichloro(methylamine) (O-ethylhydroxylamine)platinum(II) (yield: 61.1%).

Data of the above examples are summarized in the following tables 1 to 3.

TABLE 1

(Compounds represented by formula (4))

| Corresponding Compound No. | Melting Point (decomposition) (°C.) | Elemental Analysis calcd. (found) C (%) | H (%) | N (%) | Yield* (%) |
|---|---|---|---|---|---|
| 1 | 105–110 | 2.34 (2.69) | 1.57 (1.75) | 5.46 (5.37) | 58.7 |
| 2 | 117–120 | 2.34 (2.40) | 1.57 (1.32) | 5.46 (5.31) | 80.1 |
| 3 | 106–110 | 6.66 (6.51) | 2.24 (2.13) | 5.18 (5.31) | 69.4 |
| 4 | 113–115 | 12.40 (12.19) | 2.78 (2.75) | 4.82 (4.58) | 53.7 |
| 5 | 103–108 | 4.56 (4.31) | 1.91 (1.81) | 5.32 (5.31) | 68.9 |
| 6 | 105–111 | 4.56 (4.35) | 1.91 (1.76) | 5.32 (5.28) | 62.6 |
| 7 | 105–108 | 8.66 (8.61) | 2.54 (2.36) | 5.05 (4.91) | 68.9 |
| 8 | 108–113 | 6.66 (6.72) | 2.24 (2.24) | 5.18 (5.14) | 52.9 |
| 9 | 103–108 | 12.40 (12.08) | 2.78 (2.48) | 4.82 (4.78) | 59.7 |
| 10 | 115–121 | 14.27 (13.97) | 2.05 (2.01) | 4.76 (4.88) | 82.5 |
| 11 | 98–100 | 10.55 (10.47) | 2.83 (2.58) | 4.92 (4.86) | 62.9 |
| 12 | 95–100 | 10.55 (10.65) | 2.83 (2.74) | 4.92 (4.88) | 67.9 |
| 13 | 107–111 | 15.77 (15.52) | 3.31 (3.44) | 4.60 (4.77) | 86.8 |
| 14 | 108–111 | 14.08 (14.32) | 3.38 (3.32) | 4.69 (4.75) | 89.9 |

*based on the compound of formula (2)

TABLE 2

(Compounds of the Invention)

| Compound No. | Melting Point (decomposition) (°C.) | NMR (DMF-d$_7$, δ: ppm) $^{195}$Pt | $^{13}$C | Elemental analysis calcd. (%) (found (%)) C | H | N | Yield* (%) |
|---|---|---|---|---|---|---|---|
| 1 | 134–137 | −2184 | 47.8 | 3.64 (3.57) | 2.44 (2.48) | 8.49 (8.72) | 53.9 |
| 2 | 148–149 | −2249 | 62.1 | 3.64 | 2.44 | 8.49 | 64.8 |

TABLE 2-continued (Compounds of the Invention)

| Compound No. | Melting Point (decomposition) (°C.) | NMR (DMF-d$_7$, δ: ppm) $^{195}$Pt | $^{13}$C | Elemental analysis calcd. (%) (found (%)) C | H | N | Yield* (%) |
|---|---|---|---|---|---|---|---|
| | | | | (3.52) | (2.45) | (8.76) | |
| 3 | 153–155 | −2194 | 18.9, 20.0, 60.3 | 10.06 (9.84) | 3.38 (3.29) | 7.82 (7.72) | 71.5 |
| 4 | 143–145 | −2192 | 25.4, 25.4, 26.3, 29.9, 30.9, 67.6 | 18.10 (17.77) | 4.05 (4.17) | 7.03 (6.93) | 80.4 |
| 5 | 180–183 | −2242 | 13.2, 71.2 | 6.98 (6.78) | 2.93 (3.15) | 8.14 (8.08) | 77.4 |
| 6 | 158–164 | −2234 | 46.3, 59.8 | 6.98 (6.88) | 2.93 (3.00) | 8.14 (8.29) | 60.7 |
| 7 | 204–209 | −2213 | 26.2, 26.2, 26.2, 80.9 | 12.91 (13.03) | 3.79 (3.84) | 7.53 (7.18) | 83.0 |
| 8 | 166–172 | −2241 | 10.6, 21.4, 76.2 | 10.06 (9.98) | 3.38 (3.34) | 7.82 (7.84) | 72.4 |
| 9 | 177–182 | −2244 | 24.1, 24.1, 26.0, 30.7, 30.7, 81.2 | 18.10 (18.48) | 4.05 (4.20) | 7.03 (6.79) | 55.2 |

*based on the compound of formula (4)

TABLE 3

(Compounds of the Invention)

| Compound No. | Melting Point (decomposition) (°C.) | NMR (DMF-d$_7$, δ: ppm) $^{195}$Pt | $^{13}$C | Elemental analysis calcd. (%) (found (%)) C | H | N | Yield* (%) |
|---|---|---|---|---|---|---|---|
| 10 | 175–180 | −2252 | 76.5, 129.1, 129.1, 129.1, 129.7, 129.7, 136.0 | 20.70 (20.86) | 2.98 (2.88) | 6.90 (6.85) | 60.3 |
| 11 | 152–154 | −2177 | 28.3, 28.3, 28.3, 32.5, 71.5 | 15.55 (15.51) | 4.18 (4.17) | 7.25 (7.46) | 65.1 |
| 12 | 157–163 | −2301 | 13.3, 23.6, 23.6, 49.1, 70.4 | 15.55 (15.75) | 4.18 (4.22) | 7.25 (7.29) | 46.4 |
| 13 | 165–170 | −2297 | 13.3, 25.4, 25.4, 26.0, 34.5, 34.5, 55.9, 70.4 | 22.54 (22.41) | 4.73 (4.79) | 6.57 (6.83) | 64.6 |
| 14 | 155–159 | −2283 | 23.7, 23.7, 26.2, 26.2, 26.2, 49.3, 81.2 | 20.30 (20.01) | 4.87 (4.73) | 6.76 (6.89) | 63.8 |
| 15 | 189–191 | −1904 | 13.2, 15.8, 31.3, 31.3, 56.6, 70.0, 178.5, 178.6 | 23.14 (22.86) | 3.88 (3.92) | 6.75 (6.71) | 49.0 |
| 16 | 198–201 | −1903 | 10.6, 15.8, 21.5, 31.3, 31.3, 56.7, 76.0, 178.4, 178.5 | 25.18 (25.31) | 4.23 (4.11) | 6.52 (6.73) | 41.2 |
| 17 | 205–209 | −1859 | 15.7, 26.3, 26.3, 26.3, 31.2, 31.2, 56.6, 80.8, 178.4, 178.5 | 27.09 (27.24) | 4.55 (4.25) | 6.32 (6.27) | 54.8 |
| 18 | 155–160 | | | 10.06 (10.11) | 3.38 (3.18) | 7.82 (7.77) | 61.1 |

*based on the compound of formula (4)

TEST EXAMPLE 1

Antitumor effect on murine L1210 leukemia cell:

Murine L1210 leukemia cells (1×10$^5$ cells) were inoculated peritoneally into six-week-old male CDF$_1$ mice on day 0. From the next day after the inoculation, a drug (the compound of the invention or a compound for comparison) was administered peritoneally once a day for 5 days. After 30 days of observation, the percent increase in life-span (ILS) was calculated as follows:

ILS (%)=(T/C−1)×100

T: mean survival days of the drug-treated group
C: mean survival days of control group Also, an ILS$_{50}$ value (a dose which shows 50% of the ILS value by 5 administrations) was calculated from a linear regression line based on the ILS values of respective doses of each sample, and a therapeutic index (TI, TI=LD$_{50}$ value/ILS$_{50}$ value) was calculated from the LD$_{50}$ value (50% lethal dose by single peritoneally administration) obtained at the time of the dose setting. The results are shown in Tables 4 and 5. In these tables, ILS$_{max}$ means maximum ILS value (%), and corresponding dose (mg/kg) is Shown in parenthesis. In this test, cisplatin and carboplatin were respectively tested in each test lot for accurate comparison.

TABLE 4

| Compound | ILS$_{max}$ (%) | LD$_{50}$ (mg/kg) | ILS$_{50}$ (mg/kg) | | TI |
|---|---|---|---|---|---|
| Cisplatin | 88.2 | (4.0) | 18.0 | 1.3 | 13.8 |
| Carboplatin | 50.6 | (64.0) | 245.0 | 41.0 | 6.0 |
| Comparative drug A* | 97.6 | (8.0) | 31.3 | <1.0 | >31.3 |
| Compound No. 4 | >120.0 | (8.0) | 88.2 | 2.1 | 42.0 |
| Compound No. 5 | >109.4 | (4.0) | 22.1 | 0.9 | 24.6 |

*cis-dichloroammine cyclohexylamineplatinum(II)

TABLE 5

| Compound | ILS$_{max}$ (%) | LD$_{50}$ (mg/kg) | ILS$_{50}$ (mg/kg) | | TI |
|---|---|---|---|---|---|
| Cisplatin | 90.0 | (4.0) | 18.0 | 1.1 | 16.4 |
| Carboplatin | 72.5 | (64.0) | 245.0 | 33.9 | 7.2 |
| Compound No. 7 | >181.3 | (8.0) | 22.1 | 1.5 | 14.7 |
| Compound No. 8 | >131.3 | (4.0) | 11.0 | 0.8 | 13.8 |
| Compound No. 9 | 108.8 | (4.0) | 22.1 | 1.3 | 17.0 |
| Compound No. 12 | 102.5 | (8.0) | 22.1 | 1.5 | 14.7 |

TEST EXAMPLE 2

Antitumor effect on cisplatin-resistant murine L1210 leukemia cell (L1210/DDP):

The test of Test Example 1 was repeated except that cisplatin-resistant murine L1210 leukemia cell (L1210/DDP) was used instead of murine L1210 leukemia cell. The results are shown in Tables 6 and 7.

TABLE 6

| Compound | ILS$_{max}$ (%) | LD$_{50}$ (mg/kg) | ILS$_{50}$ (mg/kg) | | TI |
|---|---|---|---|---|---|
| Cisplatin | 0.9 | (4.0) | 18.0 | ND** | ND |
| Carboplatin | 8.5 | (16.0) | 245.0 | ND | ND |
| Comparative drug A* | >157.5 | (1.0) | 31.3 | <1.0 | >31.3 |
| Compound No. 4 | >183.0 | (2.0) | 88.2 | <1.0 | >88.2 |
| Compound No. 5 | >152.8 | (2.0) | 22.1 | 0.8 | 27.6 |

*cis-dichloroammine cyclohexylamineplatinum(II)
**not calculable

TABLE 7

| Compound | ILS$_{max}$ (%) | LD$_{50}$ (mg/kg) | ILS$_{50}$ (mg/kg) | | TI |
|---|---|---|---|---|---|
| Cisplatin | 5.1 | (4.0) | 18.0 | ND | ND |
| Carboplatin | 14.3 | (64.0) | 245.0 | ND | ND |
| Compound No. 7 | >206.1 | (1.0) | 22.1 | <1.0 | >22.1 |
| Compound No. 8 | >175.5 | (1.0) | 11.0 | <0.5 | >22.0 |
| Compound No. 9 | >206.1 | (1.0) | 22.1 | <1.0 | >22.1 |

TABLE 7-continued

| Compound | ILS$_{max}$ (%) | LD$_{50}$ (mg/kg) | ILS$_{50}$ (mg/kg) | | TI |
|---|---|---|---|---|---|
| Compound No. 12 | >206.1 | (2.0) | 22.1 | <1.0 | >22.1 |

TEST EXAMPLE 3

Antitumor effect on murine P388 leukemia cell:

The test of Test Example 1 was repeated except that $1\times10^6$ of murine P388 leukemia cells were used instead of $1\times10^5$ of murine L1210 leukemia cells. The results are shown in Tables 8 to 10.

TABLE 8

| Compound | ILS$_{max}$ (%) | LD$_{50}$ (mg/kg) | ILS$_{50}$ (mg/kg) | | TI |
|---|---|---|---|---|---|
| Cisplatin | >120.4 | (4.0) | 18.0 | <0.5 | >36.0 |
| Carboplatin | 73.1 | (16.0) | 245.0 | 10.5 | 23.3 |
| Comparative drug A | 101.9 | (4.0) | 31.3 | <1.0 | >31.3 |
| Compound No. 1 | >136.1 | (4.0) | 15.6 | <0.5 | >31.2 |
| Compound No. 2 | 126.9 | (4.0) | 22.1 | <0.5 | >44.2 |
| Compound No. 4 | 108.3 | (16.0) | 88.2 | 1.1 | 80.2 |
| Compound No. 5 | >129.6 | (4.0) | 22.1 | 0.6 | 36.8 |

TABLE 9

| Compound | ILS$_{max}$ (%) | LD$_{50}$ (mg/kg) | ILS$_{50}$ (mg/kg) | | TI |
|---|---|---|---|---|---|
| Cisplatin | >156.7 | (4.0) | 18.0 | <0.5 | >36.0 |
| Carboplatin | 79.8 | (32.0) | 245.0 | 12.1 | 20.2 |
| Compound No. 7 | 92.3 | (2.0) | 22.1 | <1.0 | >22.1 |
| Compound No. 8 | 101.9 | (2.0) | 11.0 | <0.5 | >22.0 |
| Compound No. 9 | 114.4 | (4.0) | 22.1 | <1.0 | >22.1 |

TABLE 10

| Compound | ILS$_{max}$ (%) | LD$_{50}$ (mg/kg) | ILS$_{50}$ (mg/kg) | | TI |
|---|---|---|---|---|---|
| Cisplatin | >120.9 | (4.0) | 18.0 | <0.5 | >36.0 |
| Carboplatin | 57.3 | (32.0) | 245.0 | 13.8 | 17.8 |
| Compound No. 15 | 93.6 | (32.0) | 176.8 | 8.2 | 21.6 |
| Compound No. 16 | 72.7 | (8.0) | 176.8 | 8.2 | 21.6 |
| Compound No. 17 | 72.7 | (32.0) | 250.0 | 12.4 | 20.2 |

Thus, it is apparent that the diamine-platinum complex (1) of the present invention has a high solubility in water and an excellent antitumor effect and therefore is useful as a malignant tumor treating drug.

While the invention has been described in detail and with reference to specific examples thereof, it will be apparent to one skilled in the art that various changes and modifications can be made therein without departing from the spirit and scope thereof.

What is claimed is:

1. A diamine-platinum complex represented by the following formula (1):

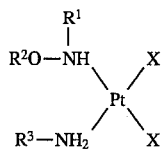

wherein $R^1$, $R^2$ and $R^3$ may be the same or different from one another, and each represents a hydrogen atom, a straight-chain or branched alkyl group, a cycloalkyl group or an aralkyl group, and X is a halogen atom, or two X groups bind to each other to form a malonic acid residue which may have a substituent, with the proviso that $R^1$, $R^2$ and $R^3$ are not hydrogen atoms at the same time.

2. The diamine-platinum complex of claim 1, wherein said alkyl group has 1 to 9 carbon atoms.

3. The diamine-platinum complex of claim 1, wherein said alkyl group is selected from methyl, ethyl, straight-chain or branched propyl, butyl, pentyl, hexyl, heptyl, octyl and nonyl groups.

4. The diamine-platinum complex of claim 1, wherein said cycloalkyl group has 3 to 9 carbon atoms.

5. The diamine-platinum complex of claim 1, wherein said cycloalkyl group is selected from cyclopropyl, cyclobutyl, cyclopentyl, cyclohexyl, cycloheptyl, cyclooctyl, and cyclononyl groups.

6. The diamine-platinum complex of claim 1, wherein said aralkyl group is selected from benzyl, 3-hydroxybenzyl, 4-hydroxybenzyl, phenetyl, diphenylmethyl, and trityl groups.

7. The diamine-platinum complex of claim 1, wherein said halogen atom is selected from fluorine, chlorine, bromine and iodine.

8. The diamine-platinum complex of claim 1, wherein said malonic acid residue is selected from those represented by the following formulae:

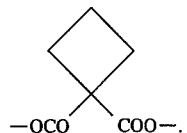

9. A pharmaceutical composition comprising the diamine-platinum complex of claim 1 and a pharmaceutically acceptable carrier.

* * * * *